United States Patent [19]

Le Baut et al.

[11] Patent Number: 4,757,067
[45] Date of Patent: Jul. 12, 1988

[54] THERAPEUTIC APPLICATION OF N-SUBSTITUTED 2-AMINOMETHYLENE-1,3-INDANEDIONES

[75] Inventors: Guillaume Le Baut, St. Sebastien sur Loire; Louis Sparfel, Reze-les-Nantes; Marie-Helene Creuzet, Bordeaux; Claude Feniou; Henri Pontagnier, both of Pessac; Gisele Prat, Talence, all of France

[73] Assignee: Societe Cortial, S.A., Paris, France

[21] Appl. No.: 5,657

[22] Filed: Jan. 21, 1987

Related U.S. Application Data

[62] Division of Ser. No. 757,499, Jul. 22, 1985.

[30] Foreign Application Priority Data

Jul. 20, 1984 [FR] France ................ 84 11678

[51] Int. Cl.⁴ ............... A61U 31/34; A61U 31/40; A61U 31/55; A61U 31/135; A61U 31/335; A61U 31/445
[52] U.S. Cl. ................ 514/213; 514/319; 514/416; 514/462; 514/472; 514/649; 514/655; 514/657
[58] Field of Search ........... 514/213, 319, 416, 472, 514/462, 649, 655, 657

[56] References Cited

PUBLICATIONS

Ozola et al. Khim. Farm. Zh (1976) 10(3) Translations, pp. 320-323 orig Chem. Abst. 85-56706g.

Primary Examiner—Stanley J. Friedman
Attorney, Agent, or Firm—Oblon, Fisher, Spivak, McClelland & Maier

[57] ABSTRACT

The present invention to pharmaceutical composition comprising an effective amount of products having the structural formula

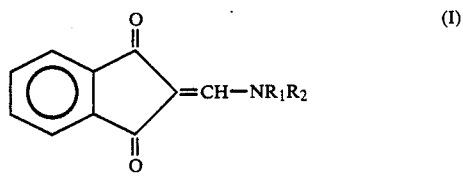

where
$R_1$ is a hydrogen atom or a lower alkyl group such as methyl or ethyl,
$R_2$ is a straight or branched cyclopropylmethyl, 2-furyl methyl, benzyl, phenyl or lower alkyl group from $C_1$ to $C_4$ such as methyl, ethyl, propyl, isopropyl, butyl, isobutyl, tertiary butyl; the $NR_1R_2$ group can also represent a nitrogenous heterocyclic compound $N(CH_2)_n$ in which n can be any value between 4 and 6.

The products are useful in human and veterinary therapy because of their anti-inflammatory, diuretic, bronchodilating, anticholinergic, antispasmodic and antidepressant properties.

20 Claims, No Drawings

THERAPEUTIC APPLICATION OF N-SUBSTITUTED 2-AMINOMETHYLENE-1,3-INDANEDIONES

This is a division of application Ser. No. 757,499, filed JULY 22, 1985.

BACKGROUND OF THE INVENTION

1. Field of the Invention

The present invention relates to N-substituted 2-aminomethylene-1,3-indanediones and their therapeutic application.

2. Discussion of the Background

The present invention relates to products having the structural formula

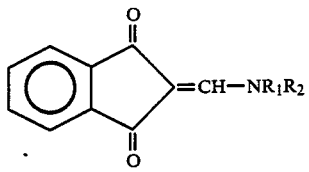

in which
- $R_1$ is a hydrogen atom or a $C_{1-6}$ group, such as, for example, methyl or ethyl,
- $R_2$ is a straight or branched cyclopropylmethyl, 2-furyl methyl, benzyl, phenyl or $C_{1-4}$ alkyl group, such as, for example, methyl, ethyl, propyl, isopropyl, butyl, isobutyl, tertiary butyl; the $NR_1R_2$ group can also represent a nitrogenous heterocyclic compound $N(CH_2)_n$, in which n can be 4, 5 or 6.

The products of the above structural formula have been previously described in the literature. Studies reported by Gasjuna, L. et al. in *Latv. P.S.R. Zinat. Akad. Vest. Kim. Ser.*, 1980, 1: 98–101, can be cited by way of example. However, no therapeutic application has been described for these derivatives.

There is a strongly felt need in the medical art for compounds possessing good pharmacological properties. For example, products having anti-inflammatory, diuretic, bronchial dilating, anticholinergic, antispasmodic and antidepressant properties are much needed in medicine.

SUMMARY OF THE INVENTION

Accordingly, it is an object of this invention to provide a novel pharmaceutical composition.

It is another object of this invention to provide a novel pharmacological composition which possesses anti-inflammatory properties.

It is another object of this invention to provide a novel pharmacological composition which possesses diuretic properties.

It is another object of this invention to provide a pharmacological composition possessing bronchial dilating properties.

It is another object of this invention to provide a novel pharmacological composition which possesses anticholinergic properties.

It is another object of this invention to provide a novel pharmacological composition which possesses antispasmodic properties.

It is another object of this invention to provide a novel pharmacological composition which possesses antidepressant properties.

It is another object of this invention to provide a novel pharmacological composition which possesses anti-inflammatory, diuretic, bronchial dilating, anticholinergic, antispasmodic or antidepressant properties and which may be used in human or veterinary therapy.

In is another object of this invention to provide a novel anti-inflammatory treatment which comprises administering an effective amount of the novel pharmaceutical composition of this invention.

It is another object of this invention to provide a novel diuretic treatment which comprises administering an effective amount of the novel pharmaceutical composition of this invention.

It is another object of this invention to provide a novel bronchial dilating treatment which comprises the administration of an effective amount of the novel pharmaceutical composition of this invention.

It is another object of this invention to provide a novel anticholinergic treatment which comprises the administration of an effective amount of the novel pharmaceutical composition of this invention.

It is another object of this invention to provide a novel antispasmodic treatment which comprises the administration of an effective amount of the novel pharmaceutical composition of this invention.

It is another object of this invention to provide a novel antidepressant treatment which comprises the administration of an effective amount of the novel pharmaceutical composition of the present invention.

Applicants have surprisingly discovered that each and every one of the above objects of this invention have been satisfied with a novel pharmacological composition containing (1) a pharmaceutically acceptable excipient, and (2) an effective amount of at least one product having the structural formula

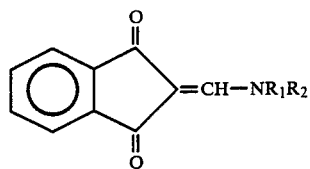

in which
- $R_1$ is a hydrogen atom or a $C_{1-6}$ alkyl group, such as methyl or ethyl;
- $R_2$ is a straight or branched cyclopropylmethyl, 2-furyl methyl, benzyl, phenyl or $C_{1-4}$ alkyl group such as, for example, methyl, ethyl, propyl, isopropyl, butyl, isobutyl, and tertiary butyl; the $NR_1R_2$ group can also be a nitrogenous heterocyclic compound $N(CH_2)_n$, wherein n may be 4, 5 or 6.

The inventors have now discovered that the products according to the formula (I) exhibit pharmacological properties, viz. of an anti-inflammatory, diuretic, bronchial dilating, anticholinergic, antispasmodic and antidepressant nature, which allows them to be used in human and veterinary therapy.

DETAILED DESCIPTION OF THE PREFERRED EMBODIMENTS

The present invention thus relates to a novel pharmacological composition which comprises (1) a pharmaceutically acceptable excipient, and (2) an effective amount of at least one product having the following structural formula

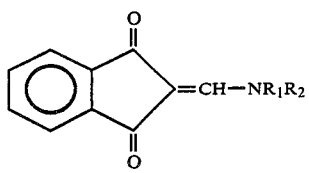

where $R_1$ is a hydrogen atom or a $C_{1-6}$ alkyl group, such as methyl or ethyl; and $R_2$ is a straight or branched cyclopropylmethyl, 2-furyl methyl, benzyl, phenyl or a $C_{1-4}$ alkyl group, such as, methyl, ethyl, propyl, isopropyl, butyl, isobutyl, or tertiary butyl; and the $NR_1R_2$ group can also be a nitrogenous heterocyclic compound $N(CH_2)_n$, where n can be 4, 5 or 6.

In a preferred embodiment of this invention the novel pharmacological composition is useful for the treatment of edema or arterial hypertension.

In another preferred embodiment of this invention, the novel pharmaceutical composition is useful for the treatment of spasmodic condition.

In another preferred embodiment, the novel pharmaceutical composition is useful as a psychotropic drug in the treatment of depressions.

In another preferred embodiment, the novel pharmaceutical composition is useful for the treatment of asthmatic conditions.

The novel pharmaceutical composition of this invention is characterized by the fact that it contains an effective amount of at least one product of formula I in combination with a pharmaceutical or veterinary vehicle or appropriate excipient.

The concentration of the product of formula I may be from $10^{-10}$M to 1M or higher. There are no particular limits to these concentrations. The only requirement which must be met in that the product of formula (I) be present in a concentration sufficiently great to provide the pharmaceutical properties of anti-inflammatory, diuretic, bronchial dialating, antidiolinergic, antipasmodic or antidepressant. Any excipent well known in this art may be used.

The products of the present invention are generally prepared by a reaction which involves 2-formyl-1,3-indanedione and an amine of the formula $NHR_1R_2$, in which $R_1$ represents a hydrogen atom or a $C_{1-6}$ alkyl group, such as methyl or ethyl; $R_2$ represents a straight or branched cyclopropylmethyl, 2-furyl methyl, benzyl, phenyl or a $C_{1-4}$ alkyl group, such as methyl, ethyl, propyl, isopropyl, butyl, isobutyl, or tertiary butyl. The $NR_1R_2$ group can also represent a nitrogenous heterocyclic compound $N(CH_2)_n$, where n may be 4, 5 or 6.

A variation of the preparation of these compounds consists of reacting 2-formyl-1,3-indanedione and the hydrochloride of the $HNR_1R_2$ amine defined above in the presence of a hydracid acceptor, such as sodium carbonate.

Other features of the invention will become apparent in the course of the following descriptions of exemplary embodiments which are given for illustration of the invention and are not intended to limiting thereof.

EXAMPLE I

2-Methylaminomethylene-1,3-indanedione. (Product of formula (I) in which $R_1=H$ and $R_2=CH_3$; code name COR3726.)

Preparation

A solution of 35 ml of ethyl orthoformate and 70 ml acetic anhydride is added to 25 g 1,3-indanedione. The mixture is heated to 80° C. for one hour. The solution is filtered and immediately cooled in an ice bath. A quantity of 130 ml of previously boiled water is added while shaking; the solution is monitored to ensure that the temperature remains at 10° C., left to crystallize in the cold for five hours, and then filtered. The yield is 67%. The precipitate is poured into 400 ml of boiling ethyl alcohol. The mixture is maintained in reflux for five minutes and then filtered into a previously heated flask. The solution contains 20 g 2-formyl-1,3-indanedione and must be used rapidly.

A solution of 1.2 g 2-formyl-1,3-indanedione in 50 ml ethyl alcohol is added to a methylamine solution in excess in 2 ml acetic acid and 50 ml ethyl alcohol. The yellow precipitate is filtered and washed in cold ethyl alcohol. The yield is 86%.

Physiochemical Properties

Melting point: 254° C. (ethyl alcohol), sublimates.

Infrared spectrum: $\gamma(CO)$ bands at 1705 and 1650 $cm^{-1}$.

NMR spectrum in DMSO ($d_6$): 9.5 ppm, singlet, 1 proton, NH; 8 ppm, singlet, 1 proton, CH; 7.73 ppm, multiplet, 4 protons, aromatic phthalyl hydrogen; 3.3 ppm, singlet, 3 protons, $CH_3$.

EXAMPLE II

2-Ethylaminomethylene-1,3-indanedione. Product of formula (I) in which $R_1=H$ and $R_2=C_2H_5$; code name COR3755.

Preparation

A quantity of 4 ml of a 70% aqueous ethylamine solution is added to a solution of 2.4 g 2-formyl-1,3-indanedione in 40 ml ethyl alcohol. The mixture is heated slightly in a water bath for 15 minutes. After cooling, the product formed precipitates. It is recrystallized in ethyl alcohol. The yield is 86.7%.

Physiochemical Properties

Melting point: 170° C. (ethyl alcohol).

NMR spectrum in $CDCl_3$: 9.33 ppm, singlet, 1 proton, NH; 8 ppm, singlet, 1 proton, CH; 7.75 ppm, multiplet, 4 protons, aromatic phthalyl hydride; 3.55 ppm, multiplet, 2 protons, $CH_2$; 1.38 ppm, triplet, 3 protons, $CH_3$.

EXAMPLE III

2-Anilinomethylene-1,3-indanedione. Product of formula (I) in which $R_1=H$ and $R_2=C_6H_5$; code name COR3756.

Preparation

Three grams of aniline is added to a solution of 2.4 g 2-formyl-1,3-indanedione in 40 ml ethyl alcohol. The mixture is heated slightly in a water bath for 20 minutes. After cooling, the product formed precipitates. It is recrystallized in ethyl alcohol. The yield s 67.1%

Physiochemical Properties

Melting point: 197° C. (ethyl alcohol).

NMR spectrum in $CDCl_3$: 11 ppm, multiplet, 1 proton, NH; 8.38 ppm, singlet, 1 proton, H at 4 on aniline; 8.13 ppm, singlet, 1 proton, CH; 7.77 ppm, multiplet, 4 protons, aromatic phthalyl hydride; 7.38 ppm, multiplet, 4 protons, H at 2,3,5,6 on aniline.

EXAMPLE IV

2-Isobutylaminomethylene-1,3-indanedione. Product of formula (I) in which $R_1=H$ and $R_2=CH_2CH(CH_3)_2$; code name COR3754.

Preparation

Three grams of isobutylamine is added to a solution of 2 g 2-formyl-1,3-indanedione in 40 ml ethyl alcohol. The The mixture is heated slightly in a water bath for 10 minutes. The ethyl alcohol is removed by evaporation and the desired product is recrystallized in ethyl alcohol. The yield is 56%.

Physiochemical Properties

Melting poing: 149° C. (ethyl alcohol).

NMR spectrum in $CDCl_3$: 9.42 ppm, singlet, 1 proton, NH; 7.93 ppm, singlet, 1 proton, =CH; 7.77 ppm, multiplet, 4 protons, aromatic phthalyl hydride; 3.3 ppm, duplet, 2 protons, $CH_2$; 1.98 ppm, multiplet, 1 proton, CH; 1.025 ppm, duplet, 6 protons, $CH_3$.

EXAMPLE V

2-Isopropylaminomethylene-1,3-indanedione. Product of formula (I) in which $R_1=H$ and $R_2=CH(CH_3)_2$; code name COR3762.

Preparation

Two milliliters of isopropylamine is added to a solution of 2.7 g 2-formyl-1,3-indanedione in 60 ml ethyl alcohol. The mixture is heated in a water bath for 30 minutes. The ethyl alcohol is removed by evaporation and the desired product is recrystallized in an isopropyl ether/ethyl alcohol (9/1) mixture and then in ethyl alcohol. The yield is 60%.

Physiochemical Properties

Melting point: 122° C. (ethyl alcohol).

NMR spectrum in $CDCl_3$: 9.3 ppm, singlet, 1 proton, NH; 8.05 ppm, singlet, 1 proton, =CH; 7.83 ppm, multiplet, 4 protons, aromatic phthalyl hydride; 3.77 ppm, multiplet, 1 proton, CH; 1.41 ppm, doublet, 6 protons, $CH_3$.

EXAMPLE VI

2-Cyclopropylmethylaminomethylene-1,3-indanedione. Product of formula (I) in which $R_1=H$ and

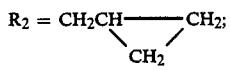

code name COR3757.

Preparation

Three grams of cyclopropylmethylamine hydrochloride and 2.9 g sodium carbonate are added to a solution of 2.4 g 2-formyl-1,3-indanedione in 40 ml ethyl alcohol. The mixture is heated in a water bath for 30 minutes and then filtered in the presence of heat. After cooling, the product formed precipitates. It is recrystallized in ethyl alcohol. The yield is 43%.

Physiochemical Properties

Melting point: 157° C. (ethyl alcohol).

NMR spectrum in $CDCl_3$: 9.47 ppm, singlet, 1 proton, NH; 8 ppm, singlet, 1 proton, =CH; 7.78 ppm, multiplet, 4 protons, aromatic phthalyl hydride; 3.37 ppm, doublet, 2 protons, $CH_2$; 1.1 ppm, multiplet, 1 proton, CH; 1.7 ppm, multiplet, 2 protons, cyclical $CH_2$; 0.38 ppm, multiple, 2 protons, cyclical $CH_2$.

EXAMPLE VII 2-(2-Furyl methylaminomethylene)-1,3-indanedione. Product of formula (I) in which $R_1=H$ and

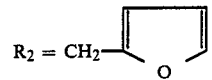

code name COR3758.

Preparation

A quantity of 2.7 g 2-furyl methylamine is added to a solution of 2.4 g 2-formyl-1,3-indanedione in 40 ml ethyl alcohol. The mixture is heated in a water bath for 20 minutes. It is subsequently filtered after cooling. The precipitate is recrystallized in dioxane. The yield is 40.4%.

Physiochemical Properties

Melting point: 216° C. (dioxane).

NMR spectrum in $CDCl_3$: 9.38 ppm, singlet, 1 proton, NH; 7.97 ppm, singlet, 1 proton, CH; 7.77 ppm, multiplet, 4 protons, aromatic phthalyl hydride; 7.5 ppm, multiplet, 1 proton, H at 5 on the furyl nucleus; 6.45 ppm, multiplet, 2 protons, H at 3 and 4 on the furyl nucleus; 4.67 ppm, singlet, 1 proton, $CH_2$; 4.53 ppm, singlet, 1 proton, $CH_2$.

EXAMPLE VIII

2-Piperidinomethylene-1,3-indanedione. Product of formula (I) in which $NR_1R_2=N(CH_2)_5$; code name COR3759.

Preparation

A quantity of 2.5 g piperidine is added to a solution of 2.4 g 2-formyl-1,3-indanedione in 40 ml ethyl alcohol. The mixture is heated in a water bath for 20 minutes. It is subsequently filtered after cooling. The precipitate is recrystallized in ethyl alcohol. The yield is 44%.

Physiochemical Properties

Melting point: 167° C. (ethyl alcohol).

NMR spectrum in $CDCl_3$: 7.77 ppm, multiplet, 4 protons, aromatic phthalyl hydride; 7.6 ppm, singlet, 1 proton, CH; 4.53 ppm, multiplet, 2 protons, $CH_2$ at 2 or 6 on the piperidine nucleus; 3.67 ppm, multiplet, 2 protons, $CH_2$ at 2 or 6 on the piperidine nucleus; 1.83 ppm, multiplet, 6 protons, $CH_2$ at 3, 4 and 5 on the piperidine nucleus.

EXAMPLE IX

2-Dimethylaminomethylene-1,3-indanedione. Product of formula (I) in which $R_1=R_2=CH_3$; code name COR3761.

Preparation

Five milliliters of a 25% dimethylamine solution in ethyl alcohol is added to a solution of 2.7 g 2-formyl-1,3-indanedione in 60 ml ethyl alcohol. The mixture is heated at approximately 40° C. for four hours. The solvent is removed by evaporation. The precipitate is isolated, then recrystallized in a mixture of isopropyl ether/ethyl alcohol (8/2). The yield is 58%.

Physiochemical Properties

Melting point: 138° C. (ethyl alcohol).

MNR spectrum in $CDCl_3$: 7.8 ppm, multiplet, 4 protons, aromatic phthalyl hydride; 7.6 ppm, singlet, 1 proton, =CH; 3.93 ppm, singlet, 3 proton, $CH_3$; 3.42 ppm, singlet, 3 protons, $CH_3$.

EXAMPLE X

1-Perhydroazepinyl-2-methylene-1,3-indanedione.
Product of formula (I) in which $NR_1R_2=N(CH_2)_6$; code name COR3790.

Preparation

Three milliliters hexamethylenimine is added to a solution of 1.6 g 2-formyl-1,3-indanedione in 40 ml ethyl alcohol. The mixture is heated in a water bath form 60 minutes. The ethyl alcohol is partially evaporated. The residue is refrigerated for 12 hours. The precipitate is filtered and then purified by passing over a silica column using ethyl ether as the eluent. The yield is 43%.

Physiochemical Properties

Melting point: 125° C. (ethyl alcohol).

IR spectrum: $\gamma CO$ bands at 1700 and 1650 cm$^{-1}$.

NMR spectrum in CDCl$_3$: 7.78 ppm, multiplet, 4 protons, aromatic phthalyl hydride; 7.63 ppm singlet, 1 proton, CH; 4.50 ppm, multiplet, 2 protons, CH$_2$ at 2 or 7 on the perhydroazepinyl nucleus; 3.67 ppm, multiplet, 2 protons, CH$_2$ at 3, 4, 5 and 6 on the perhydroazepinyl nucleus.

The results of the toxicological and pharmacological studies performed on the products according to the present invention are reported below.

Toxicity

COR3726, COR3754, COR3755, COR3756, COR3757, COR3758, COR3759, COR3761, and COR3790 caused no deaths in mice in an oral dose of 300 mg/kg or an intraperitoneal dose of 200 mg/kg. When administered to mice orally, dissolved in 20% Tween, COR3761 exhibited an LD$_{50}$ of 520 (457–592) mg/kg.

Pharmacology

Diuretic activity was determined in several experimental models. In rats subjected to excess water intake, COR376 and COR3761, administered in an oral dose of 20 mg/kg, increased urinary sodium excretion by a factor of 4.4 and 3.5, respectively. Spironolactone administered under the same conditions and in the same dose increased sodium excretion by 3.6. When given orally to rats subjected to excess sodium chloride intake, COR3761 produced the following increments in volumetric urinary excretion measured at the sixth hour: 10% in a dose of 10 mg/kg, 42.5% in a dose of 20 mg/kg and 68.4% in a dose of 40 mg/kg. COR3761 was administered to rats subjected to excess water intake and volumetric urinary excretion and sodium and potassium elimination were measured over a period of six hours. These parameters were, respectively, −13%, +73%, +77% after administration of 10 mg/kg; +9%, +241%, +114% after 20 mg/kg and −4%, +532%, +138% after 40 mg/kg. The sodium/potassium ratio which was 0.4 in the control animals was 0.47 at 10 mg/kg, 0.62 at 20 mg/kg and 1.48 at 40 mg/kg. In the course of another experiment, volumetric urniary excretion and sodium and potassium elimination were, respectively: +1%, +100%, +54% at 20 mg/kg; +10%, +313%, +69% at 40 mg/kg and +16%, +356% and +89% at 60 mg/kg. The sodium/potassium ratio went from 0.43 in the control animals to 0.53 at 20 mg per kg, 1.02 at 40 mg/kg and 1.12 at j60 mg/kg.

Spasmolytic activity was determined in vitro by measurement of the effect of the test product on ileum contractions in guinea pigs induced by transmural electric transmission in an oxygenated Krebs solution at 32° C. When used in a concentration of 0.5 mcg/ml, COR3754 and COR3759 inhibited these contractions by 50%. Domperidone exhibits the same activity in a concentration of 1 mcg/ml.

Anti-inflammatory activity was determined in rats by measurement of inhibition of the edema induced by intraplantar injection of 0.1 ml of a 1% carragheenin suspension. The test products were administered orally one hour before the carragheenin injection and the determination was made three hours after injection. Doses of 100 mg/kg COR3755 and COR3761 produced 36% and 49% inhibition, respectively. Aspirin administered under the same conditions in a dose of 150 mg/kg produced 40% inhibition of the edema.

Bronchodilating activity was determined in vitro by measurement of the flow of Tyrode's solution through an isolated and perfused guinea pig lung which had been contracted by addition of 0.05 mcg/ml methacholine to the perfusion liquid. COR3755, COR3757, COR3759, COR3761, COR3762 and COR3790, which were used, respectively, in concentrations of 50, 100, 10, 10, 25 and 100 mcg/ml, increased the flow by 50%. Aminophylline produces this same effect in a concentration of 100 mcg/ml.

Anticholinergic activity was evaluated by measurement of the contractions induced by 0.1 mcg/ml acetylcholine in isolated segments of guinea pig ileum. When used in concentrations of 100, 50, 10, 50, 10 and 25 mcg/ml, respectively, COR3755, COR3757, COR3761, COR3762 and COR3790 produced an 80% inhibition of these contractions.

Central anticholinergic activity was evaluated by measurement of inhibition, under the test product, of muscular tremors induced in mice by subcutaneous injection of 0.5 mg/kg oxotremorine. The tremors are rated according to an index ranging from 0 to 6, one hour after intraperitoneal injection of the test product. An index of 0 indicates absence of tremor while 6 represents maximum tremor. COR3762 administered in a dose of 100 mg/kg resulted in an index of 3; imipramine, given under the same conditions in a dose of 25 mg/kg produced the same activity.

Antidepressant activity was determined in the test involving potentiation of yohimbine toxicity and in the test involving inhibition of reserpine-induced ptosis.

One hour before oral administration of the test product, a non-lethal dose of yohimbine, i.e., 15 mg/kg-doses of COR3761 and COR3762 produced 80% and 100% mortality, respectively.

Mice were given an oral dose of the test product ninety minutes before intraperitoneal injection of 5 mg/kg dissolved reserpine. Ptosis was evaluated according to an index of 0 to 6, where 0 signifies ptosis and 6 indicates absence of ptosis. Under the experimental conditions, COR3761 and COR3762 in doses of 200 and 50 mg/kg, respectively, produces respective ratings of 5 and 4.

In view of their pharmacological activity, which is associated with low toxicity, the products of the present invention can be used in human or veterinary therapy.

When combined with the conventional vehicles, they can e.g., be utilized in the treatment of cardiac, renal or hepatic edema and arterial hypertension, in the treatment of spasmodic symptoms, especially of the digestive and respiratory systems, in the treatment of asthma conditions or for depressive states.

When combined with the conventional vehicles, depending on the indication, they can be administered e.g., by the oral route in the form of dragees, tables, syrups, vials; rectally in the form of suppositories; by the intramuscular route or the intravenous route. According to the indication and the subject, dodes administered range from 1-100 mg/day given in one to six administrations orally, from 1-100 mg/day given in one or two administrations rectally and from 0.5-50 mg given by parenteral injection.

Obviously, numerous modifications and variations of the present invention are possible in light to the above teachings. It is therefore to be understood that within the scope of the appended claims, the invention may be practiced otherwise than as specifically described herein.

What is claimed as new and desired to be secured by Letters Patent of the United States is:

1. A method for treating edema, comprising administering to a host suffering from edema a pharmaceutical composition comprising:
   (i) a pharmaceutically effective quantity of at least one product having the following structural formula:

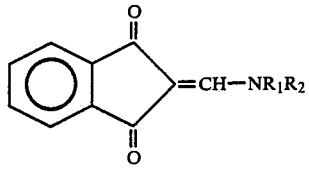

wherein:
   $R_1$ is a hydrogen atom or $C_{1-6}$ alkyl group; and
   $R_2$ is a straight or branched $C_{1-4}$ alkyl group, a cyclopropylmethyl group, a 2-furyl methyl group, a benzyl group, or a phenyl group; or
   $NR_1R_2$ is a nitrogenous heterocyclic compound $N(CH_2)_n$ where n is 4, 5, or 6; and
   (ii) a pharmaceutically or veterinarily acceptable excipient.

2. The method of claim 1, wherein $R_1$ is a hydrogen atom and $R_2$ is a 2-furyl methyl group.

3. The method of claim 1, wherein $NR_1R_2$ is $N(CH_2)_4$.

4. The method of claim 1, wherein $NR_1R_2$ is $N(CH_2)_5$.

5. The method of claim 1, wherein $NR_1R_2$ is $N(CH_2)_6$.

6. A method for treating depression, comprising administering to a host suffering from depression a pharmaceutical composition comprising:
   (i) a pharmaceutically effective quantity of at least one product having the following structural formula:

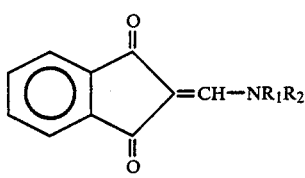

wherein:
   $R_1$ is a hydrogen atom or a $C_{1-6}$ alkyl group; and
   $R_2$ is a straight or a branched $C_{1-4}$ alkyl group, a cyclopropylmethyl group, a 2-furyl methyl group, a benzyl group, or a phenyl group; or
   $NR_1R_2$ is a nitrogenous heterocyclic compound $N(CH_2)_n$, where n is 4, 5 or 6; and
   (ii) a pharmaceutically or veterinarily acceptable excipient.

7. The method of claim 6, wherein $R_1$ is a hydrogen atom and $R_2$ is a 2-furyl methyl group.

8. The method of claim 6, wherein $NR_1R_2$ is $N(CH_2)_4$.

9. The method of claim 6, wherein $NR_1R_2$ is $N(CH_2)_5$.

10. The method of claim 6, wherein $NR_1R_2$ is $N(CH_2)_6$.

11. A method for treating asthmatic conditions, comprising administering to a host suffering from an asthmatic condition a pharmaceutical comprising:
    (i) a pharmaceutically effective quantity of at least one product having the following structural formula:

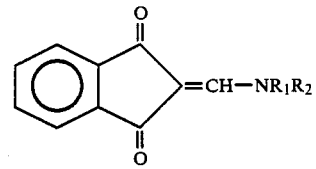

wherein:
   $R_1$ is a hydrogen atom or a $C_{1-6}$ alkyl group; and
   $R_2$ is a straight or branched $C_{1-4}$ alkyl group, a cyclopropylmethyl group, a 2-furyl methyl group, a benzyl group, or a phenyl group; or
   $NR_1R_2$ is a nitrogenous heterocyclic compound $N(CH_2)_n$, where n is 4, 5 or 6; and
   (ii) a pharmaceutically or veterinarily acceptable excipient.

12. The method of claim 11, wherein $R_1$ is a hydrogen atom and $R_2$ is a 2-furyl methyl group.

13. The method of claim 11, wherein $NR_1R_2$ is $N(CH_2)_4$.

14. The method of claim 11, wherein $NR_1R_2$ is $N(CH_2)_5$.

15. The method of claim 11, wherein $NR_1R_2$ is $N(CH_2)_6$.

16. A pharmaceutical composition, comprising:
    (i) a pharmaceutically effective quantity of at least one product having the following structural formula:

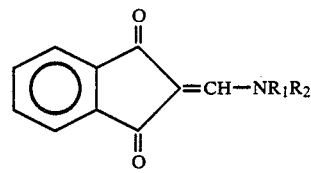

wherein
   $R_1$ is a hydrogen atom and $R_2$ is a 2-furyl methyl group; or
   $NR_1R_2$ is $N(CH_2)_4$, $N(CH_2)_5$ or $N(CH_2)_6$; and
   (ii) a pharmaceutically or veterinarily acceptable excipient.

17. The pharmaceutical composition of claim 16, wherein $R_1$ is a hydrogen atom and $R_2$ is a 2-furyl methyl group.

18. The pharmaceutical composition of claim 16, wherein $NR_1R_2$ is $N(CH_2)_5$.

19. The pharmaceutical composition of claim 16, wherein $NR_1R_2$ is $N(CH_2)_6$.

20. The pharmaceutical composition of claim 16, wherein $NR_1R_2$ is $N(CH_2)_4$.

* * * * *